(12) United States Patent
Kang et al.

(10) Patent No.: US 9,897,539 B2
(45) Date of Patent: Feb. 20, 2018

(54) APPARATUS AND METHOD FOR MEASURING DEPOSITION RATE

(71) Applicant: SAMSUNG DISPLAY CO., LTD., Yongin-si, Gyeonggi-Do (KR)

(72) Inventors: Tae Min Kang, Suwon-si (KR); Seung Mook Lee, Suwon-si (KR); Young Suk Cho, Seoul (KR)

(73) Assignee: Samsung Display Co., Ltd., Yongin-si, Gyeonggi-do (KR)

( * ) Notice: Subject to any disclaimer, the term of this patent is extended or adjusted under 35 U.S.C. 154(b) by 0 days.

(21) Appl. No.: 14/860,888

(22) Filed: Sep. 22, 2015

(65) Prior Publication Data

US 2016/0245745 A1     Aug. 25, 2016

(30) Foreign Application Priority Data

Feb. 25, 2015   (KR) .................. 10-2015-0026801

(51) Int. Cl.
   *G01F 1/00*      (2006.01)
   *G01N 21/53*     (2006.01)
   *C23C 14/54*     (2006.01)

(52) U.S. Cl.
   CPC .......... *G01N 21/53* (2013.01); *C23C 14/544* (2013.01); *G01F 1/00* (2013.01)

(58) Field of Classification Search
   CPC . G01F 1/74; G01F 1/64; G01F 1/7042; G01F 1/00; G01N 23/12
   See application file for complete search history.

(56) References Cited

U.S. PATENT DOCUMENTS

| | | | |
|---|---|---|---|
| 4,381,894 A | | 5/1983 | Gogol, Jr. et al. |
| 4,676,639 A | * | 6/1987 | Van Wagenen ........ G01N 21/65 356/246 |
| 5,754,297 A | | 5/1998 | Nulman |
| 5,835,230 A | * | 11/1998 | McAndrew ............... G01J 3/42 250/341.5 |
| 5,880,823 A | | 5/1999 | Lu |
| 6,075,588 A | * | 6/2000 | Pinsukanjana ..... G01N 21/3103 356/325 |
| 6,669,824 B2 | * | 12/2003 | Sferlazzo .............. C23C 14/044 118/723 FI |
| 8,613,520 B2 | * | 12/2013 | Anderson ............ G01N 21/031 359/581 |
| 2004/0008435 A1 | * | 1/2004 | Takahashi .......... G01B 11/0616 359/883 |

(Continued)

FOREIGN PATENT DOCUMENTS

| | | |
|---|---|---|
| JP | 05-306459 A | 11/1993 |
| KR | 10-0732709 B1 | 6/2007 |

*Primary Examiner* — David Porta
*Assistant Examiner* — Mamadou Faye
(74) *Attorney, Agent, or Firm* — Lee & Morse, P.C.

(57) ABSTRACT

An apparatus for measuring a deposition rate includes a light source unit in a deposition region between a deposition source and a substrate in a vacuum chamber, the light source unit emits a monochromatic light toward a deposition material released from the deposition source, a photosensor unit that measures at least one of light absorption, scattering, and emission in the deposition region when light emitted from the light source unit passes through the deposition region, and a multi-pass forming unit defining a multi-pass path between the light source unit and the photosensor unit.

19 Claims, 6 Drawing Sheets

(56) References Cited

U.S. PATENT DOCUMENTS

| | | | |
|---|---|---|---|
| 2004/0080050 A1* | 4/2004 | McMillin | H01J 37/32963 257/758 |
| 2004/0150827 A1* | 8/2004 | Potyrailo | G01N 21/643 356/432 |
| 2005/0173375 A1* | 8/2005 | Mitrovic | H01J 37/32972 216/60 |
| 2011/0212256 A1* | 9/2011 | Beck | C23C 14/0623 427/10 |
| 2014/0273295 A1* | 9/2014 | Li | H01L 22/12 438/7 |

* cited by examiner

US 9,897,539 B2

APPARATUS AND METHOD FOR MEASURING DEPOSITION RATE

CROSS-REFERENCE TO RELATED APPLICATION

Korean Patent Application No. 10-2015-0026801, filed on Feb. 25, 2015, in the Korean Intellectual Property Office, and entitled: "Apparatus and Method for Measuring Deposition Rate," is incorporated by reference herein in its entirety.

BACKGROUND

1. Field

The present disclosure relates to an apparatus and a method for measuring a deposition rate. More particularly, the present disclosure relates to an apparatus and a method for measuring a deposition rate which may be used in an actual deposition region by an optical method using at least one of absorption, scattering, and emission strength of light due to a deposition material, may be semi-permanently used, and may have high measurement accuracy.

2. Description of the Related Art

An organic light emitting diode (OLED) is a next generation display element which generates an emission phenomenon from an organic thin film by implementing the organic thin film and a metal electrode of multi layers on a glass substrate, on which a transparent electrode is applied, and applying voltage thereto, and is expected to be established as a display after a LCD. In particular, the organic thin film may be formed in a thin film form by depositing organic material gas, which is evaporated by heating a crucible including an organic material within a high vacuum chamber, on a glass substrate.

The OLED is manufactured by stacking a multi-layered thin film, e.g., the organic thin film and a metal thin film, on a substrate. An OLED facility for forming such thin films by deposition mainly uses a cluster scheme in which a plurality of unit chambers are connected, and is configured to transfer and convey the substrate and perform an element process in a state in which the substrate is horizontally disposed between the respective deposition chambers.

For example, a vacuum deposition method may form a thin film by installing at least one deposition source at a lower portion of a vacuum chamber, and a substrate to be processed, which is a deposition substrate, at an upper portion of the vacuum chamber. Such an apparatus for forming an organic thin film may use a vacuum exhaust system connected to the vacuum chamber so as to keep an inside of the vacuum chamber at a predetermined vacuum state, and then evaporate a deposition material from at least one deposition source at the predetermined vacuum state. For example, the deposition source may include a crucible having an organic material, which is a thin film material, accommodated therein, and a heater which is wound around the crucible to electrically heat the crucible. Therefore, when the crucible is heated with the increase in temperature of the heater, the organic material is evaporated.

The above information disclosed in this Background section is only for enhancement of understanding of embodiments, and therefore, it may contain information that does not form the prior art that is already known in this country to a person of ordinary skill in the art.

SUMMARY

An exemplary embodiment of the present disclosure provides an apparatus for measuring a deposition rate, the apparatus including a light source unit in a deposition region between a deposition source and a substrate in a vacuum chamber, the light source unit emits a monochromatic light toward a deposition material released from the deposition source, a photosensor unit that measures at least one of light absorption, scattering, and emission in the deposition region when light emitted from the light source unit passes through the deposition region; and a multi-pass forming unit defining a multi-pass path between the light source unit and the photosensor unit.

The apparatus may further include a controller to control positions of the light source unit and the photosensor unit, to allow an optical axis of each of the light source unit and the photosensor unit to be positioned at a center of the deposition region, and to calculate the deposition rate based on at least one of the light absorption, scattering, and emission measured by the photosensor unit as follows, transmitted light, scattered light, PL emission strength=k·C, wherein k is a constant, and C is a concentration of the deposition material.

The multi-pass forming unit may be a light shielding wall enclosing the deposition region to allow the light emitted from the light source unit to be wave-guided to the photosensor unit, the multi-pass forming unit including an inner mirror surface, and first and second wave-guide openings which face each other and are provided with the light source unit and the photosensor unit.

The apparatus may further include a light collecting unit facing the light source unit and the photosensor unit, a center of the light collecting unit being at an optical axis of the light source unit.

The light collecting unit may be a concave mirror outside the multi-pass forming unit, the concave mirror having a larger curvature than the multi-pass forming unit.

The apparatus may further include a light pass increasing unit passing the light emitted from the light source unit through the deposition region several times to increase a light path.

The light pass increasing unit may include first to fourth reflection mirrors defining four corners, the first to fourth reflection mirrors defining first and second light passes intersecting a center of the deposition region, and the light source unit and the photosensor unit may be installed in back of two of the first to fourth reflection mirrors, the light source unit and the photosensor being on a same side of the multi-pass forming unit.

The light source unit may be a UV light source, and the photosensor unit may measure intensity of light again emitted from the deposition material absorbing the light emitted from the light source unit, the photosensor unit including an optical filter unit that filters only emission by the light source unit in front of the photosensor unit.

The optical filter unit may be a UV cut-off filter, and further includes a band pass filter in front of the light source unit and filters light having a wavelength of a specific band.

The apparatus may further include a light source strength modulator periodically changing intensity of the light source unit, wherein the optical filter unit filters only a signal component having a same period.

Another exemplary embodiment of the present disclosure provides a method for measuring a deposition rate, the method including disposing a light source unit and a photosensor unit to face each other within a vacuum chamber of an evaporator, such that a deposition region between a deposition source and a processed substrate is between the light source unit and the photosensor unit, emitting light from the light source toward the deposition region, detecting light emitted from the light source, after passing through the deposition region, by the photosensor unit, and measuring at least one of light absorption, scattering, and emission, after detection by the photosensor unit, wherein the deposition rate is calculated as follows, transmitted light, scattered light, PL emission strength=k·C, wherein k is a constant, and C is a concentration of a deposition material evaporated from the deposition source.

The method may further include forming a light pass of a multi pass between the light source unit and the photosensor unit, and forming a light shielding wall enclosing the deposition region, such that a region between the light source unit and the photosensor unit is light-shielded.

Forming the light pass of the multi pass between the light source unit and the photosensor unit may include collecting the light emitted from the light source unit to concave mirrors facing each other, and transmitting the collected light to the photosensor unit installed on a same side as the light source unit.

The method may further include installing the concave mirror outside a concentric circle which connects the light source unit with the photosensor unit.

Forming the light pass of the multi pass between the light source unit and the photosensor unit may include reflecting the light emitted from the light source unit and passing the reflected light through the deposition region several times.

The method may further include installing first to fourth reflection mirrors to form first and second light passes intersecting a center of the deposition region.

The method may further include installing an optical filter unit passing through only light having a specific wavelength in front of the light source unit or the photosensor unit.

The method may further include filtering, by the optical filter unit, a signal component having a same period by periodically converting intensity of the light source unit.

The optical filter may use a UV cut-off filter when the photosensor unit measures emission.

BRIEF DESCRIPTION OF THE DRAWINGS

Features will become apparent to those of ordinary skill in the art by describing in detail exemplary embodiments with reference to the attached drawings, in which.

DETAILED DESCRIPTION

Figure 1:
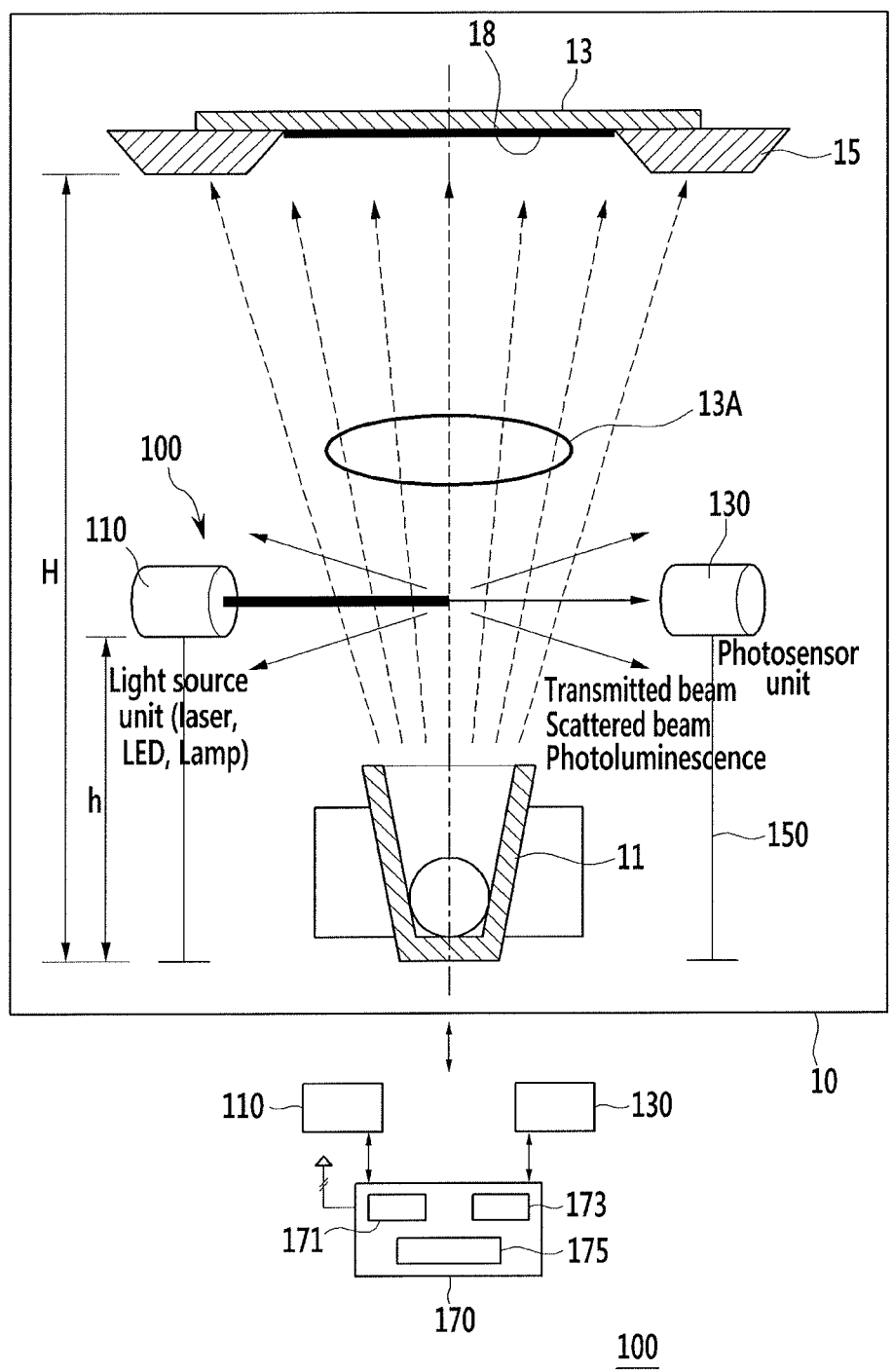
FIG. 1 illustrates a conceptual diagram of an apparatus for measuring a deposition rate according to an exemplary embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the following detailed description, an apparatus for measuring a deposition rate according to an exemplary embodiment has been shown and described, simply by way of illustration. As those skilled in the art would realize, the described embodiments may be modified in various different ways, all without departing from the spirit or scope of the present disclosure. Accordingly, the drawings and description are to be regarded as illustrative in nature and not restrictive. Like reference numerals designate like elements throughout the specification.

Further, in the drawing figures, the dimensions of layers and regions may be exaggerated for clarity of illustration. It will also be understood that when a layer or element is referred to as being "on" another layer or substrate, it can be directly on the other layer or substrate, or intervening layers or elements may also be present. In addition, it will also be understood that when a layer or element is referred to as being "between" two layers or elements, it can be the only layer or element between the two layers or elements, or one or more intervening layers or elements may also be present.

FIG. 1 illustrates a conceptual diagram of an apparatus 100 for measuring a deposition rate according to an exemplary embodiment.

As illustrated in FIG. 1, a vacuum chamber 10 of a vacuum evaporator uses an apparatus 100 for measuring a deposition rate according to an exemplary embodiment, a deposition source 11 disposed at a bottom portion of the vacuum chamber 10 with a deposition material accommodated therein and a heater provided at an outside thereof, and a processed substrate 13 over the deposition source 11 and deposited with a deposition material 18 vaporized or sublimated from the deposition source 11. The apparatus 100 for measuring a deposition rate has a center disposed in a deposition region 13A of the vacuum chamber 10 between the deposition source 11 and the processed substrate 13.

An organic light emitting diode (OLED) generates an emission phenomenon from an organic thin film by forming the organic thin film with several layers and a metal electrode on a glass substrate, on which a transparent electrode is applied, and applying voltage thereto. Further, the organic thin film is formed in a thin film form by depositing organic material gas, which is evaporated by heating a crucible including an organic material in a high vacuum chamber, on the glass substrate.

In a general OLED, an intermediate layer including at least an emission layer is formed between electrodes facing each other, and may be provided with various layers. For example, the intermediate layer may include a hole injection layer, a hole transportation layer, an emission layer, an electron transportation layer, an electron injection layer, and the like, and is an organic thin film made of an organic material.

The organic material that is used to form the organic thin film is heated in the deposition source 11 of the vacuum chamber 10 to an evaporation point (or a sublimation point), and the evaporated organic material is released from the deposition source 11 to be coated on the processed substrate 13. For example, a physical vapor deposition (PVD) process may implement the deposition source 11 with a crucible having high heat resistance and chemical safety within the vacuum chamber 10.

In a process of manufacturing the OLED, the electrodes which are disposed on and beneath the intermediate layer may be formed by a deposition method using the deposition apparatus of the present disclosure, and other wirings may be formed by the deposition method of the present disclosure. A material of the electrode and the wiring of the OLED is generally evaporated at high temperature and depends on the kind of material used. For example, magnesium is evaporated at about 500° C. to about 600° C., silver is evaporated at about 1000° C. or more, aluminum is evaporated at about 1000° C., and lithium is evaporated at about 300° C.

Referring back to FIG. 1, the apparatus 100 for measuring a deposition rate may include a photosensor unit 130, a light source unit 110, a multi-pass forming unit 150, and a controller 170.

The photosensor unit 130 measures absorption, scattering, photoluminescence, and the like, which appear due to deposited material molecules when the light emitted from the light source unit 110, e.g., a laser, a light emitting diode (LED), a lamp, and the like, passes through the deposition region 13A. For example, the light source unit 110 emits light through the deposition region 13A, so the photosensor unit 130 measures light intensity from the light source unit 110, after the light passes through, e.g., and is affected by, the deposition region 13A.

The multi-pass forming unit 150 is installed outside the deposition region 13A to enable the photosensor unit 130 to measure absorption spectrum of the multi-pass between the light emitted from the light source unit 110 and the deposition material. The controller 170 controls the light source unit 110 and the photosensor unit 130 to precisely measure a deposition speed in the multi-pass by using the absorption, the scattering, the photoluminescence, and the like which are measured by the photosensor unit 130, and to accurately calculate the deposition rate by performing a predetermined correction using the multi-pass measurement value.

For example, since the material of the electrode and the wiring of the OLED is generally evaporated at high temperature, when a lamp is used as the light source unit 110, the temperature may be set to be about 300° C. or less which is equal to or less than the evaporation temperature. In another example, when a laser is used as the light source unit 110, as illustrated in Table 1 below, the laser may have a wavelength of about 200 nm to about 400 nm, i.e., a wavelength in which absorbance for aluminum, copper, and the like, is good.

TABLE 1

Absorbance depending on laser wavelength

| Material | KrF excimer (248 nm) | Argon ion (500 nm) | Ruby (694 nm) | Yttrium aluminum garnet (1064 nm) | Carbon dioxide (10.6 μm) |
|---|---|---|---|---|---|
| Aluminum | 18 | 9 | 11 | 10 | 1.9 |
| Copper | 70 | 56 | 17 | 8 | 1.5 |
| Iron | 60 | 68 | 64 | 35 | 3.5 |
| Nickel | 58 | 40 | 32 | 26 | 5 |
| Titanium |  | 48 | 45 | 42 | 8 |
| White paint |  | 30 | 20 | 10 | 90 |

As described above, a reduction in strength, i.e., intensity, of light transmitted through the deposition region 13A is measured by passing monochromatic light having a sufficiently large absorption coefficient through the deposition material to be measured. Therefore, the photosensor 130 measures the concentration of only the deposition material to be measured without interference with other deposition materials.

As further illustrated in FIG. 1, the controller 170 may include a position controller 171 controlling the light source unit 110 and disposed at a measurement distance h up to a deposition region A most suitable to measure the absorption, the scattering, the photoluminescence, and the like of the light emitted from the light source unit 110 which appear due to the deposited material molecules, and at a distance H from the processed substrate 13. It is noted that the distance H is also the distance between the deposition source 11 and the processed substrate 13. Further, the controller may include a horizontal controller 173 accurately measuring focus, and the like of the photosensor unit 130 for the light source unit 110, and a calculator 175 accurately calculating the deposition speed by using the measurement value of the photosensor unit 130 and performing the predetermined correction and conversion.

Meanwhile, the multi-pass forming unit 150 may be disposed so that a center of the photosensor unit 130 is positioned at the optical axis of the light source unit 110 for accurately measuring the focus, and the like of the light source unit 110, and the photosensor unit 130 with respect to a frame 15 and may be disposed so that the positions of the light source unit 110 and the photosensor unit 130 are linked with each other, thereby better facilitating the position control.

That is, when the light emitted from the light source units 110, e.g., a laser or a LED lamp, passes through the deposition region 13A toward the center of the photosensor unit 130, the absorption, the scattering, PL emission, and the like are generated due to the deposited material molecules in the deposition region 13A. Therefore, interaction between the emitted light and the deposition material in the deposition region 13A is proportional to the concentration of the material molecules, as represented by the following Relational Expression 1, where k is a constant and C is concentration of deposited material.

$$\text{Transmitted light, scattered light, } PL \text{ emission strength} = k \cdot C \quad \text{[Relational Expression 1]}$$

Therefore, the photosensor unit 130 may measure a size of the interaction between the light and deposition material to find out the concentration of the deposition material, i.e., the deposition rate. The measurement is the strength (absorbance) of the transmitted light, the strength of the scattered light, and the PL emission strength in the case of using a UV light source.

Hereinafter, an apparatus for measuring a deposition rate according to first to fifth modification embodiments of the present disclosure will be described with reference to FIGS. 2 to 6.

Figure 2:
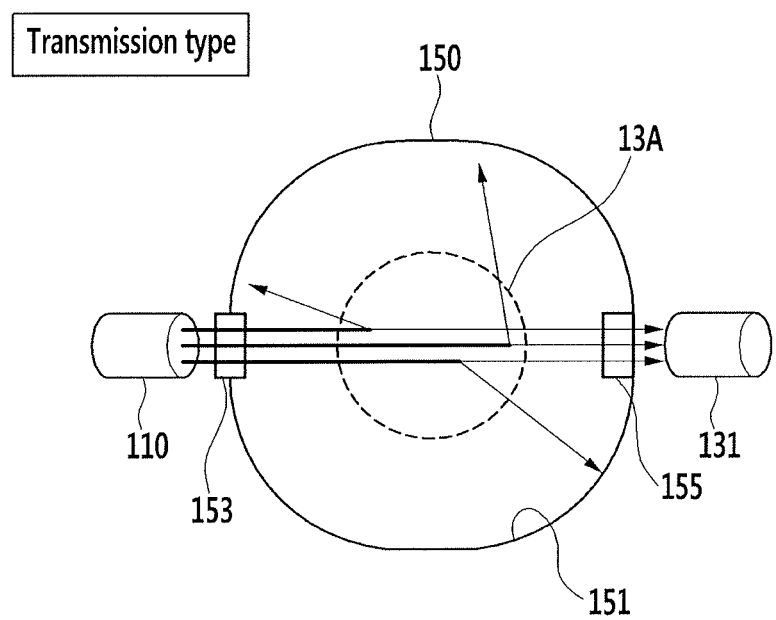
FIG. 2 illustrates a conceptual diagram of an apparatus for measuring a deposition rate according to a first modification embodiment of the exemplary embodiment.

As illustrated in FIG. 2, in the apparatus 100 for measuring a deposition rate according to the first modification embodiment of the present disclosure, the light source unit 110 is a laser having high transmittance. Further, the photosensor unit 130 may be an absorbance sensor 131 which measures the absorbance of light by the deposition material when the light emitted from the light source unit 110 passes through the deposition region 13A, thereby measuring the strength of the transmitted light.

A beam measured by the absorbance sensor 131 removes a scattered beam scattered by colliding with the deposition material from a beam incident from the light source unit 110, as expressed by the relational expression 2 below.

Measured beam=incident beam−scattered beam (Relational Expression 2)

The controller 170 may convert the strength (absorbance) of the transmitted light into an electric signal to derive the deposition speed of the deposition material using the intensity of the electric signal.

However, gas molecules each have a property which optionally absorbs only energy corresponding to vibration energy quantum and generally absorbs light of an infrared region as the vibration energy. Therefore, it is preferable to use the light of the infrared region of the light source unit 110. For this reason, $CO_2$, CO, $CH_4$, $C_3H_8$, and the like each have a unique absorption spectrum for infrared rays. For example, $CO_2$ absorbs a wavelength of 4.25 CO absorbs a wavelength of 4.7 μm, and $CH_4$ absorbs a wavelength of 3.3 μm, and absorbance of light varies depending on a concentration of the corresponding gas.

Therefore, the light source unit 110 may generate light having only a specific wavelength band and may also generate light having a band different from the specific wavelength band. The light source unit 110 may be, e.g., a LED and a laser diode (LD), tungsten, glove, Nernst glove, a far-infrared high pressure mercury vapor lamp, and the like.

In this case, absorption $A(\lambda)$, which is the absorbance of light in any wavelength, is defined by the following Beer-Lambert Equation (Equation 1).

$$A(\lambda)=E(\lambda)bC \qquad \text{Equation 1}$$

Here, $A(\lambda)$ represents absorbance, $E(\lambda)$ represents an absorption coefficient, b represents a transmission distance, and C represents the concentration of the deposition material. The absorption coefficient $E(\lambda)$ is a function of the wavelength λ, and therefore a wavelength at which the absorption coefficient $E(\lambda)$ is large is selected and thus the absorbance $A(\lambda)$ may be increased. Meanwhile, the absorbance $A(\lambda)$ is proportional to the transmission distance b of light and the coefficient of the deposition material. Therefore, to increase the proportional degree of the absorbance $A(\lambda)$ and the concentration C of the deposition material, it is preferable to make a value of the transmission distance b large. Further, the absorbance $A(\lambda)$ has the following Equation 2.

$$A(\lambda)=-\log [I(\lambda)/I_0(\lambda)] \qquad \text{Equation 2}$$

In Equation 2 above, $I_0(\lambda)$ represents strength of reference light, and $I(\lambda)$ represents strength of measured light. It may be appreciated that the concentration of the deposition material by measuring the strength $I(\lambda)$ of light in the state in which the strength $I_0(\lambda)$ of reference light, the absorption coefficient $E(\lambda)$, and the transmission distance b are known.

Further, the absorption coefficient $E(\lambda)$ is a function of the wavelength (λ), and therefore, the reduction in strength of transmitted light is measured by passing the monochromatic light having the sufficiently large absorption coefficient $E(\lambda)$ through the deposition material to be measured to measure only the concentration of gas to be measured without being interfered by other deposition materials.

According to the Beer-Lambert's law, it may be appreciated that the absorption of light (represents absorbance $A(\lambda)$ in the above Equations 1 and 2) is proportional to the concentration C of the deposition material and the transmission distance b of light. To increase the absorption of light, there is a need to increase the transmission length b. In this case, however, a length of the apparatus is long and a physical length of appearance of a mechanism is increased correspondingly.

According to the first modification embodiment of the present disclosure, the multi-pass forming unit 150 may be a light shielding wall performing a guidance function to wave-guide the light emitted from the light source unit 110 to the photosensor unit 130 so as to increase a light path without increasing the length. An inner surface of the light shielding wall may form a mirror surface 151 to reflect light.

To minimize a loss and diffused reflection of light when the light is reflected, in the case in which the light shielding wall is metal, the mirror surface 151 may also be subjected to a mirror surface treatment by performing surface polishing on the metal, and may also be formed by coating gold, nickel, silver, copper, or a double layer of gold/chromium which have high reflectance.

When the multi-pass forming unit 150 is cut in a ground direction, a cross section may have any suitable shape, e.g., a circle or a polygon. Meanwhile, the multi-pass forming unit 150 may be further provided with first and second wave-guide openings 153 and 155 which are disposed to face each other, and are provided with the light source unit 110 and the photosensor unit 130, respectively. As such, the first and second wave-guide openings 153 and 155 which are disposed to face each other are provided with the light source unit 110 and the photosensor unit 130, thereby better facilitating the position control.

Components of a second modification embodiment of the present disclosure are almost similar to those of the first modification embodiment of the present disclosure, but the second modification embodiment of the present disclosure is different from the first modification embodiment of the present disclosure in that a light collecting unit 140 is further installed to increase a ratio of absorption/scattering when the concentration of the absorbed/scattered deposition material is small and the photosensor unit 130 measures light collected by the light collecting unit 140.

Figure 3:
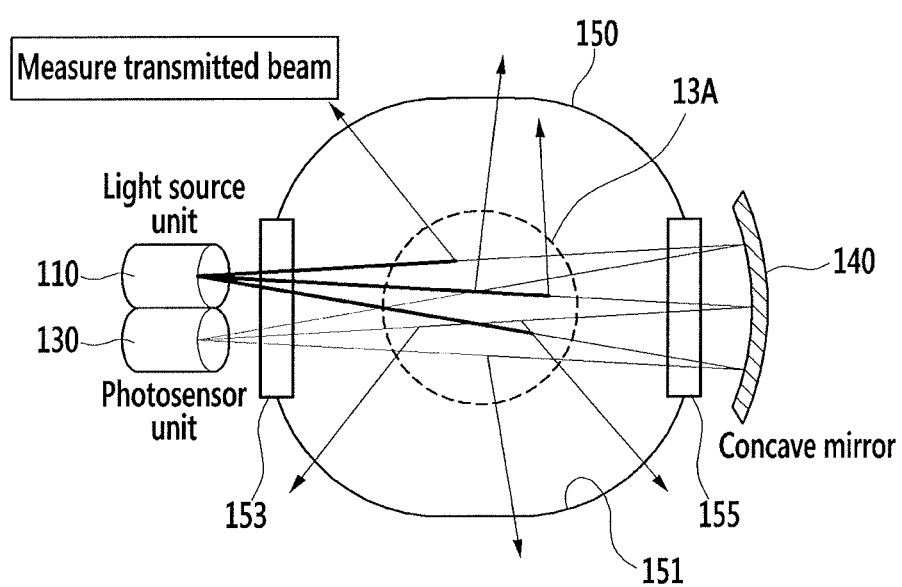
FIG. 3 illustrates a schematic diagram of an apparatus for measuring a deposition rate according to a second modification embodiment of the exemplary embodiment.

As illustrated in FIG. 3, according to the second modification embodiment of the present disclosure, the light collecting unit 140 may be a concave mirror and is disposed at a position facing the light source unit 110 so that a center thereof is disposed at the optical axis of the light source unit 110. In this case, the photosensor unit 130 may be disposed to be parallel with the light source unit 110 to measure light collected after the reflected beam passes through the deposition region again by using the concave mirror.

The concave mirror is installed outside the multi-pass forming unit 150 to have a larger curvature, and thus, collects light passing through the second wave-guide opening 155 of the multi-pass forming unit 150 to expand a light collecting area. As a result, it is possible to accurately perform the measurement by making the ratio of absorption/scattering of the deposition material for the light emitted from the light source unit 110 large by using a concave mirror.

Components of a third modification embodiment of the present disclosure are almost similar to those of the first modification embodiment of the present disclosure, but the third modification embodiment of the present disclosure is different from the first modification embodiment of the present disclosure in that a light pass increasing unit 157 is further installed to pass light through the deposition region several times so as to prevent light transmittance from being reduced due to the deposition material such as absorption/ scattering, and the like. The photosensor unit 130 measures the measurement beam passing through the light pass increasing unit 157.

Figure 4:
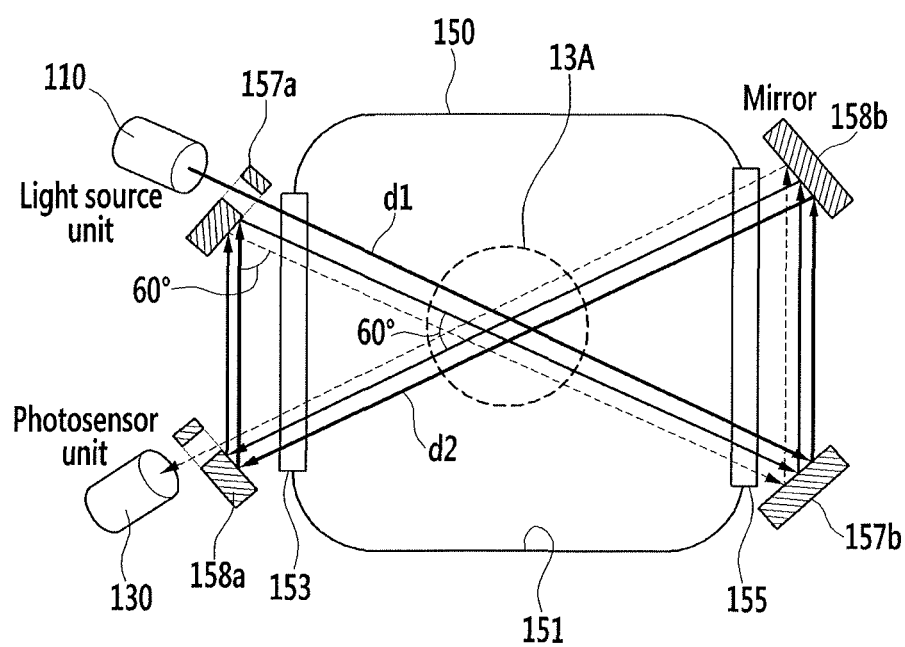
FIG. 4 illustrates a schematic diagram of an apparatus for measuring a deposition rate according to a third modification embodiment of the exemplary embodiment.

As illustrated in FIG. 4, according to the third modification exemplary embodiment of the present disclosure, the light collecting unit 140 may be disposed on the same side as the light source unit 110 and the photosensor unit 130 so that the light emitted from the light source unit 110 passes through a first reflection mirror 157a and the center of the deposition region 13A and is reflected from a second reflection mirror 157b, and the reflected light again passes through a third reflection mirror 158b and the center of the deposition region 13A and then is incident on the photosensor unit 130 through a fourth reflection mirror 158a. The first to fourth reflection mirrors 157a, 157b, 158a, and 158b may be installed so that the light pass, i.e., light path, may be circulated.

A first light pass d1 formed by the first and second reflection mirrors 157a and 157b, and a second light pass d2 formed by the third and fourth reflection mirrors 158a and 158b intersect the center of the deposition region 13A. A center of the first reflection mirror 157a near the light source unit 110 and a center of the fourth reflection mirror 158a near the photosensor unit 130 are disposed to be inclined by about 60° to the first light pass d1, such that the light pass may be substantially infinitely increased. Similarly, the second reflection mirror 157b and the third reflection mirror 158b are disposed to have a predetermined angle with the second light pass d2.

As a result, the light may pass through the deposition region several times by using the first to fourth reflection mirrors 157a and 157b which are installed at four corners. Thus, the deposition speed and the measurement accuracy of the deposition material may be increased.

An apparatus for measuring a deposition rate according to another exemplary embodiment of the present disclosure and a modification embodiment will be described with reference to FIGS. 5 and 6.

Figure 5:
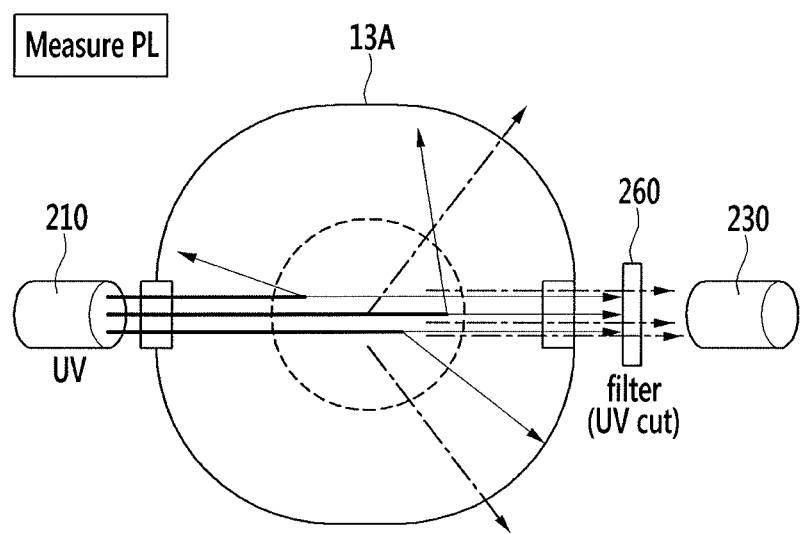
FIG. 5 illustrates a schematic diagram of an apparatus for measuring a deposition rate according to another exemplary embodiment.

FIG. 5 is a schematic diagram for describing a configuration of an apparatus for measuring a deposition rate according to another exemplary embodiment of the present disclosure. FIG. 6 is a conceptual diagram for describing an apparatus for measuring a deposition rate according to a first modification embodiment of the embodiment of FIG. 5.

An apparatus 200 for measuring a deposition rate according to another exemplary embodiment of the present disclosure measures the photoluminescence (PL) emission strength of the deposition material, which is stimulated by the light emitted from a light source unit 210 to emit light by itself, thereby measuring the concentration of the deposition material. A representative example of emission may include fluorescence or phosphorescence, which is a phenomenon that the light absorbed from the surrounding is emitted again. In this case, a wavelength of the emitted light is equal to or longer than that of the absorbed light.

As illustrated in FIG. 5, in the apparatus 200 for measuring a deposition rate, the light source unit 210, a photosensor unit 230 which measures the strength of light again emitted by absorbing the light emitted from the light source unit 210, and an optical filter unit 260 which measures only the PL emitted from the light source unit 210 are installed to face the center of the deposition region 13A.

The light source unit 210 may be a UV light source which is suitable to generate the fluorescence or the phosphorescence. The optical filter unit 260 installed in front of the photosensor unit 230 may be a UV cut-off filter to measure only the PL generated by the light source unit 210 which is the UV light source.

Figure 6:
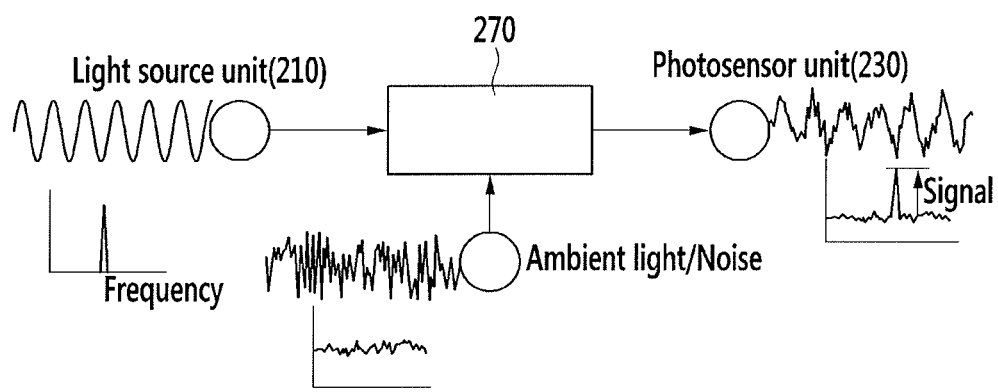
FIG. 6 illustrates a conceptual diagram of an apparatus for measuring a deposition rate according to a modification embodiment of the other exemplary embodiment.

Meanwhile, as illustrated in FIG. 6, in the apparatus 200 for measuring a deposition rate according to a first modification embodiment, a light source strength modulator 270, which periodically changes the strength of the light source unit 210, may be installed in front of the light source unit 210 to prevent an effect of ambient light. In this case, the optical filter unit 260 installed in front of the light source unit 210 filters only a signal component having the same period from a light receiving signal. Therefore, the photosensor unit 230 measures the strength of light, thereby increasing the accuracy in the measurement. Meanwhile, when the light source unit 210 itself does not generate only a wavelength of a specific band, a band pass filter may be further installed in front of the light source unit 210 to emit light having the wavelength of the specific band.

By way of summation and review, when organic material is evaporated within a vacuum chamber of a conventional deposition apparatus, the organic material may be deposited on a crystal sensor within the vacuum chamber, thereby damaging the function of the crystal sensor. As such, a thickness and a deposition speed of the organic thin film, which is measured by the crystal sensor, may not be properly measured. Further, while attempts have been made to install the crystal sensor in a non-deposition region of the vacuum chamber of the conventional deposition apparatus so as not to cover the deposition region, spatial limitations occur.

In contrast, example embodiments provide an apparatus and a method for measuring a deposition rate which may be used in an actual deposition region, may be semi-permanently used, and may have high measurement accuracy. In particular, example embodiments provide a light source unit and a photosensor unit that are outside, e.g., peripheral to, the deposition region, while a multi-pass between the light source unit and the photosensor unit overlaps the deposition regions to allow measurement of light absorption, scattering, and emission in the deposition region.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An apparatus for measuring a deposition rate, comprising:
a light source adjacent a deposition region between a deposition source and a substrate in a vacuum chamber, the light source to emit a monochromatic light toward the deposition region;
a photosensor that measures at least one of light absorption, scattering, and emission in the deposition region when light emitted from the light source passes through the deposition region; and
a multi-pass forming area defining a multi-pass path between the light source and the photosensor during a deposition process, the photosensor to output a signal indicative of at least one of the light absorption, scattering, and emission in the deposition region during the deposition process, the signal corresponding to the deposition rate, wherein the multi-pass forming area is in the vacuum chamber between the deposition source and the substrate and enclosing the deposition region, and wherein the light source, the photosensor, and the multi-pass forming area are in the vacuum chamber.

2. The apparatus as claimed in claim 1, further comprising:
a controller to control positions of the light source and the photosensor, to allow an optical axis of each of the light source and the photosensor to be positioned at a center of the deposition region, and to calculate the deposition rate based on at least one of the light absorption, scattering, and emission measured by the photosensor as follows, in accordance with measured parameters, by the photosensor:

transmitted light,scattered light, or emission strength=$k \cdot C$, wherein k is a constant, and C is a concentration of the deposition material.

3. The apparatus as claimed in claim 1, wherein the multi-pass forming area includes a light shielding wall in the vacuum chamber enclosing the deposition region to allow the light emitted from the light source to be wave-guided to the photosensor, the multi-pass forming area including an inner mirror surface, and first and second wave-guide openings which face each other and are provided with the light source and the photosensor.

4. The apparatus as claimed in claim 1, further comprising a light collector in the vacuum chamber facing the light source and the photosensor, a center of the light collecting collector being at an optical axis of the light source.

5. The apparatus as claimed in claim 4, wherein the light collector is a concave mirror outside the multi-pass forming unit, the concave mirror having a larger curvature than the multi-pass forming area.

6. The apparatus as claimed in claim 1, further comprising a light pass increasing unit in the vacuum chamber passing the light emitted from the light source through the deposition region several times to increase a light path.

7. The apparatus as claimed in claim 6, wherein:
the light pass increasing unit includes first to fourth reflection mirrors defining four corners, the first to fourth reflection mirrors defining first and second light passes intersecting a center of the deposition region, and
the light source and the photosensor are installed in back of two of the first to fourth reflection mirrors, the light source and the photosensor being on a same side of the multi-pass forming area.

8. The apparatus as claimed in claim 1, wherein:
the light source is a UV light source, and
the photosensor measures intensity of light again emitted from the deposition material absorbing the light emitted from the light source, the photosensor including an optical filter that filters only emission by the light source in front of the photosensor.

9. The apparatus as claimed in claim 8, wherein the optical filter is a UV cut-off filter, and further includes a band pass filter in front of the light source and filters light having a wavelength of a specific band.

10. The apparatus as claimed in claim 8, further comprising
a light source strength modulator periodically changing intensity of the light source, wherein the optical filter filters only a signal component having a same period.

11. A method for measuring a deposition rate, the method comprising:
disposing a light source and a photosensor to face each other within a vacuum chamber of an evaporator, such that a deposition region between a deposition source and a processed substrate is between the light source and the photosensor;
forming a multi pass area of light between the light source and the photosensor during a deposition process, wherein the multi pass is in the vacuum chamber enclosing the deposition region;
emitting light from the light source toward the deposition region;
detecting light emitted from the light source, after passing through the deposition region, by the photosensor; and
measuring at least one of light absorption, scattering, and emission, after detection by the photosensor and during the deposition process, wherein the deposition rate is calculated as follows in accordance with measured parameters by the photosensor:

transmitted light,scattered light, or emission strength=$k \cdot C$, wherein k is a constant, and C is a concentration of a deposition material evaporated from the deposition source.

12. The method as claimed in claim 11, wherein forming the light pass of a multi pass between the light source and the photosensor includes providing a light shielding wall enclosing the deposition region in the vacuum chamber, such that a region between the light source and the photosensor is light-shielded and light is waveguided to the photosensor.

13. The method as claimed in claim 12, wherein forming the light pass of the multi pass between the light source and the photosensor includes:
collecting the light emitted from the light source using a concave mirror facing the light source; and
transmitting the collected light to the photosensor installed on a same side as the light source.

14. The method as claimed in claim 13, further comprising
installing the concave mirror outside a concentric circle which connects the light source with the photosensor.

15. The method as claimed in claim 11, wherein forming the light pass of the multi pass between the light source and the photosensor includes reflecting the light emitted from the light source and passing the reflected light through the deposition region several times.

16. The method of as claimed in claim 15, further comprising installing first to fourth reflection mirrors to form first and second light passes intersecting a center of the deposition region.

17. The method as claimed in claim 11, further comprising installing an optical filter passing through only light having a specific wavelength in front of the light source or the photosensor.

18. The method as claimed in claim 17, further comprising filtering, by the optical filter, a signal component having a same period by periodically converting intensity of the light source.

19. The method as claimed in claim 17, wherein the optical filter uses a UV cut-off filter when the photosensor measures emission.

* * * * *